United States Patent
Harris et al.

(10) Patent No.: US 10,011,682 B2
(45) Date of Patent: Jul. 3, 2018

(54) METHOD OF PREPARING CARBOXYLIC ACID FUNCTIONALIZED POLYMERS

(71) Applicant: Nektar Therapeutics, San Francisco, CA (US)

(72) Inventors: J. Milton Harris, Huntsville, AL (US); Antoni Kozlowski, Huntsville, AL (US); Lihong Guo, Plano, TX (US)

(73) Assignee: NEKTAR THERAPEUTICS, San Francisco, CA (US)

( * ) Notice: Subject to any disclaimer, the term of this patent is extended or adjusted under 35 U.S.C. 154(b) by 0 days.

(21) Appl. No.: 13/922,020

(22) Filed: Jun. 19, 2013

(65) Prior Publication Data

US 2013/0281634 A1 Oct. 24, 2013

Related U.S. Application Data

(63) Continuation of application No. 13/279,134, filed on Oct. 21, 2011, now abandoned, which is a continuation of application No. 13/023,960, filed on Feb. 9, 2011, now Pat. No. 8,067,505, which is a continuation of application No. 10/982,303, filed on Nov. 4, 2004, now abandoned.

(60) Provisional application No. 60/517,794, filed on Nov. 6, 2003.

(51) Int. Cl.

| | |
|---|---|
| C08G 63/91 | (2006.01) |
| C08G 65/332 | (2006.01) |
| C08G 65/334 | (2006.01) |
| A61K 31/765 | (2006.01) |
| C08F 251/00 | (2006.01) |
| C08F 261/04 | (2006.01) |
| C08F 265/00 | (2006.01) |
| C08F 271/00 | (2006.01) |
| C08F 283/06 | (2006.01) |
| C08F 289/00 | (2006.01) |
| C08F 291/00 | (2006.01) |
| C08G 65/30 | (2006.01) |

(52) U.S. Cl.
CPC ............ *C08G 63/91* (2013.01); *A61K 31/765* (2013.01); *C08F 251/00* (2013.01); *C08F 261/04* (2013.01); *C08F 265/00* (2013.01); *C08F 271/00* (2013.01); *C08F 283/06* (2013.01); *C08F 289/00* (2013.01); *C08F 291/00* (2013.01); *C08G 65/30* (2013.01); *C08G 65/332* (2013.01); *C08G 65/3322* (2013.01); *C08G 65/3346* (2013.01)

(58) Field of Classification Search
None
See application file for complete search history.

(56) References Cited

U.S. PATENT DOCUMENTS

| | | | |
|---|---|---|---|
| 4,421,930 A | 12/1983 | Van Paassen et al. | |
| 4,721,579 A | 1/1988 | Kim | |
| 5,278,303 A | 1/1994 | Krepinsky et al. | |
| 5,279,921 A * | 1/1994 | Onishi et al. ............. | 430/270.1 |
| 5,483,008 A | 1/1996 | Sakurai et al. | |
| 5,605,976 A * | 2/1997 | Martinez et al. ............. | 525/408 |
| 5,672,662 A | 9/1997 | Harris et al. | |
| 5,681,567 A | 10/1997 | Martinez et al. | |
| 5,922,675 A | 7/1999 | Baker et al. | |
| 5,932,462 A | 8/1999 | Harris et al. | |
| 6,326,514 B1 | 12/2001 | Klug et al. | |
| 6,362,254 B2 | 3/2002 | Harris et al. | |
| 6,448,369 B1 | 9/2002 | Bentley et al. | |
| 8,067,505 B2 | 11/2011 | Harris et al. | |
| 2002/0156047 A1 | 10/2002 | Zhao | |
| 2004/0019157 A1 | 1/2004 | Won | |
| 2005/0214250 A1 | 9/2005 | Harris et al. | |
| 2011/0130539 A1 | 6/2011 | Harris et al. | |
| 2012/0041155 A1 | 2/2012 | Harris et al. | |

FOREIGN PATENT DOCUMENTS

| | | |
|---|---|---|
| EP | 0 824 126 | 2/1998 |
| JP | 10087815 | 4/1998 |
| WO | WO 98/41562 | 9/1998 |
| WO | WO 2004/013205 | 2/2004 |

OTHER PUBLICATIONS

Gehrhardt, Soluble Polymers in Organic Chemistry; Polymer Bulletin 18; 1987; pp. 487-493.*
Buckmann, et al., "Functionalization of Poly(ethylene glycol) and Monomethoxy-Poly(ethylene glycol)," Makromol. Chem., vol. 182, pp. 1379-1384, (1981).
Fradet, et al., "Synthesis of Monocarboxylic Polyoxyethylenes," Polymer Bulletin, vol. 4, pp. 205-210, (1981).
Gehrhardt, et al., "Soluble polymers in organic chemistry 5. Preparation of carboxyl- and amino-terminal polyethylene glycol of low molecular weight," Polymer Bulletin, vol. 18, pp. 487-493, (1987).

(Continued)

*Primary Examiner* — David J Buttner
(74) *Attorney, Agent, or Firm* — Susan T. Evans; Mark A. Wilson

(57) ABSTRACT

Methods for preparing water soluble, non-peptidic polymers carrying carboxyl functional groups, particularly carboxylic acid functionalized poly(ethylene glycol) (PEG) polymers are disclosed, as are the products of these methods. In general, an ester reagent R(C=O)OR', wherein R' is a tertiary group and R comprises a functional group X, is reacted with a water soluble, non-peptidic polymer POLY-Y, where Y is a functional group which reacts with X to form a covalent bond, to form a tertiary ester of the polymer, which is then treated with a strong base in aqueous solution, to form a carboxylate salt of the polymer. Typically, this carboxylate salt is then treated with an inorganic acid in aqueous solution, to convert the carboxylate salt to a carboxylic acid, thereby forming a carboxylic acid functionalized polymer.

11 Claims, No Drawings

(56) References Cited

OTHER PUBLICATIONS

Harris, et al., "Synthesis and Characterization of Poly(ethylene glycol) Derivatives," J. of Poly. Sci.: Poly. Chem. Ed., vol. 22, pp. 341-352, (1984).
Donbrow, "Stability of the Polyoxyethylene Chain," Nonionic Surfactants: Phys. Chem., Editor: Martin J. Schick; Marcell Dekker, ISBN 0824775309, (1987).
Pine, Organic Chemistry, 4th edition, pp. 320-323, (1980).
Topchiyeva, "Synthesis of Biologically Active Polyethylene Glycol Derivatives. A Review.," Polymer Sci., U.S.S.R., vol. 32, No. 5, pp. 833-851, (1990).
Veronese, et al., "Preparation, Physico-Chemical and Pharmacokinetic Characterization of Monomethoxypoly(Ethylene Glycol)-Derivatized Superoxide Dismutase," J. of Controlled Rel., vol. 10, pp. 145-154, (1989).
PCT International Search Report corresponding to PCT Application No. PCT/US2004/036850 dated Apr. 18, 2005.
PCT International Preliminary Report on Patentability corresponding to PCT Application No. PCT/US2004/036850 dated May 8, 2006.
Australian Examiner's First Report corresponding to Australian Patent Application No. 2004289992 dated Nov. 24, 2008.
Chinese First Office Action corresponding to Chinese Patent Application No. 200480039882.7 dated Mar. 14, 2008.
Chinese Second Office Action corresponding to Chinese Patent Application No. 200480039882.7 dated Mar. 20, 2009.
European Communication corresponding to European Patent Application No. 04810369.1 dated Feb. 16, 2007.
European Communication corresponding to European Patent Application No. 04810369.1 dated Nov. 20, 2007.
European Communication corresponding to European Patent Application No. 04810369.1 dated Feb. 24, 2009.
Israeli Examination Report corresponding to Israeli Patent Application No. 175406 dated Jul. 6, 2009.
Mexican Examination Report corresponding to Mexican Patent Application No. PA/a/2006/005082 dated Aug. 21, 2009.
Enzon Enzon Pharmaceuticals, Macromolecular Engineering Technologies, pp. 1-14, (2004).
Nektar™—Transforming Therapeutics, Nektar Molecule Engineering: Polyethylene Glycol and Derivatives for Advanced PEGylation, pp. 1-20, Catalog—2003, (Jul. 2003).
Nektar™—Transforming Therapeutics, Nektar Advanced PEGylation: Polyethylene Glycol and Derivatives for Advanced PEGylation, pp. 1-24, Catalog—2004, (Jul. 2004).
NOF Corporation, "PEG Derivatives, Phospholipid and Drug Delivery Materials for Pharmaceuticals", pp. 1-46, Catalogue 2003—1st, (Jan. 2003).
NOF Corporation, "PEG Derivatives, Phospholipid and Drug Delivery Materials for Pharmaceuticals", pp. 1-50, Catalogue 2003—2nd, (Mar. 2004).
Polypure, Products; PEG amines; PEG acids and amino acids; PEG thiols and disulfides; Biotins, (Apr. 2004).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Shearwater Polymers, Inc., Polyethylene Glycol and Derivatives, pp. 1-49, (Catalog—Mar. 1995).
Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).
United States Office Action corresponding to U.S. Appl. No. 10/982,303 dated Jan. 4, 2007.
United States Office Action corresponding to U.S. Appl. No. 10/982,303 dated Aug. 6, 2007.
United States Office Action corresponding to U.S. Appl. No. 10/982,303 dated Jan. 23, 2008.
United States Office Action corresponding to U.S. Appl. No. 10/982,303 dated Oct. 9, 2008.
United States Office Action corresponding to U.S. Appl. No. 10/982,303 dated Feb. 2, 2009.
United States Office Action corresponding to U.S. Appl. No. 10/982,303 dated Apr. 24, 2009.
United States Office Action corresponding to U.S. Appl. No. 10/982,303 dated Dec. 1, 2009.
United States Office Action corresponding to U.S. Appl. No. 10/982,303 dated Jul. 13, 2010.
Japan Notice of Reasons for Rejection corresponding to Japanese Patent Application No. 2006-539659 mailing date Oct. 5, 2010.
Canadian Office Action corresponding to Canadian Patent Application No. 2,544,697 dated Jun. 21, 2011.
Indian First Examination Report corresponding to Indian Patent Application No. 1553/CHENP/2006 dated Aug. 17, 2010.
Korean Office Action corresponding to Korean Patent Application No. 2006-7008804 dated Sep. 6, 2011.
Patent Abstracts of Japan—abstract of JP06-135889, no date.
Harris, et al., "Pegylation: A Novel Process for Modifying Pharmacokinetics", Clin. Pharmacokinet, vol. 40, No. 7, pp. 539-551, (2001).
Roberts, et al., Chemistry for peptide and protein PEGylation; Advanced Drug Delivery Reviews; vol. 54; pp. 459-476 (2002).
Zalipsky, "Functionalized Poly(ethylene glycol) for Preparation of Biologically Relevant Conjugates", Bioconjugate Chem., vol. 6, pp. 150-165, (1995).
Harris, "Laboratory Synthesis of Polyethylene Glycol Derivatives", JMS-REV. Macromol. Chem. Phys., C25(3), pp. 325-373, (1985).
Zalipsky et al., "Use of Functionalized Poly(Ethylene Glycol)s for Modification of Polypeptides", Polyethylene Glycol Chemistry, Biotechnical and Biomedical Applications, edited by J. Milton Harris, Plenum Press, New York, (1992).
Johansson, "Effects of Poly(Ethylene Glycol)-Bound Alcohols and Amines on the Partition of Albumins and Thylakoid Membranes in an Aqueous Two-Phase System", Journal of Chromatography, vol. 368, pp. 309-317, (1986).

* cited by examiner

METHOD OF PREPARING CARBOXYLIC ACID FUNCTIONALIZED POLYMERS

CROSS-REFERENCE TO RELATED APPLICATIONS

This application is a continuation application of U.S. patent application Ser. No. 13/279,134, filed Oct. 21, 2011, now abandoned, which is a continuation application of U.S. patent application Ser. No. 13/023,960, filed Feb. 9, 2011, now U.S. Pat. No. 8,067,505, which is a continuation application of U.S. patent application Ser. No. 10/982,303, filed Nov. 4, 2004, now abandoned, which claims the benefit of priority under 35 U.S.C. §119(e) to U.S. Provisional Patent Application Ser. No. 60/517,794, filed Nov. 6, 2003, all of which are incorporated herein by reference in their entireties.

FIELD OF THE INVENTION

This invention relates to methods for preparing water soluble, non-peptidic polymers carrying carboxyl functional groups, particularly carboxylic acid functionalized polyethylene glycol) (PEG)polymers.

BACKGROUND OF THE INVENTION

Poly(ethylene glycol) (PEG) derivatives activated with electrophilic groups are useful for coupling to nucleophilic groups, such as amino groups, of biologically active molecules. In particular, active esters and other carboxylic acid derivatives of PEG have been used to attach PEG to proteins bearing amino groups.

PEG molecules having terminal carboxymethyl groups have been described, for example, by Martinez et al., U.S. Pat. No. 5,681,567, Veronese et al., Journal of Controlled Release 10:145-154 (1989), and Buckmann et al., Makromol. Chem. 182(5): 1379-1384 (1981). U.S. Pat. No. 5,672,662 (Harris et al.) discloses PEG derivatives having a terminal propionic or butanoic acid moiety. Such carboxyl-terminated PEGs are used to prepare active esters suitable for conjugation to proteins or other molecules bearing amino groups.

However, a persistent problem associated with preparation of carboxyl-functionalized polymers has been the difficulty in obtaining the desired polymer product at a sufficiently high purity level. For example, Veronese et al. and Buckmann et al., cited above, employ a method of synthesizing mPEG carboxylic acids which comprises converting mPEG-OH to an ethyl ester of mPEG carboxylic acid, by base-catalyzed reaction of mPEG-OH with an α-halo ethyl ester, followed by base-promoted hydrolysis of the ester. However, this approach provides mPEG acids of only about 85% purity, with the main contaminant being mPEG-OH, which cannot be separated from the mPEG carboxylic acid using typical purification methods such as precipitation, crystallization or extraction. Removal of mPEG-OH requires the use of preparative ion exchange column chromatography, which is time consuming and expensive. PEG carboxylic acids obtained commercially frequently contain residual amounts of PEG-OH, which complicates the preparation of derivatives or bioconjugates based on these materials.

U.S. Pat. Nos. 5,278,303, 5,605,976 and 5,681,567 report the preparation of PEG carboxylic acids containing little or no starting material (PEG alcohol) by employing a tertiary alkyl haloacetate to prepare a tertiary alkyl ester-functionalized PEG, which is then hydrolyzed with acid, preferably trifluoroacetic acid (TFA).

Various treatises on the use of protecting groups note that tertiary alkyl esters, such as t-butyl esters, are stable to mild base hydrolysis typically used to hydrolyze primary alkyl esters, such as ethyl esters. Strong base hydrolysis could cause cleavage of carboxylic acid groups. See, for example, T. W. Greene, Protective Groups in Organic Synthesis, $3^{rd}$ edition, 1999, p. 406; or P. J. Kocienski, Protecting Groups, 1994, p. 125. Accordingly, these tertiary alkyl esters are conventionally cleaved with acid, typically with TFA.

However, use of trifluoroacetic acid can result in purification and product stability problems. Trifluoroacetic acid is difficult to completely remove from the final carboxyl-functionalized polymer, particularly the amount of TFA suggested in the above-referenced patents. The presence of residual trifluoroacetic acid results in poor product stability, due to degradation of the polymer caused by acid-promoted autoxidation. See, for example, M. Donbrow, "Stability of the Polyoxyethylene Chain", in Nonionic Surfactants: Physical Chemistry, M. J. Schick, ed., Marcel Dekker, 1987, pp. 1011 ff. This article reports that acids catalyze the formation of hydroperoxides and hydroperoxide rupture, leading to cleavage of polyoxyethylene chains.

Although U.S. Pat. No. 5,605,976 suggests distillation as a means for separating organic materials from the polymer product, even compounds with very low boiling points are difficult to remove from high molecular weight polymers using a distillation process, and the difficulty increases as the molecular weight of the polymer increases.

There is a need in the art for alternative methods for preparing carboxylic acid functionalized polymers in high yield and free from significant amounts of polymer contaminants, particularly the polymer starting material. There is also a need in the art for alternative synthesis methods that do not utilize reagents that are either difficult to remove from the final polymer product or cause product stability problems.

SUMMARY OF THE INVENTION

In one aspect, the invention provides a method for preparing a water soluble, non-peptidic polymer functionalized with a carboxyl group, the method comprising:

(i) reacting an ester reagent R(C=O)OR', where R' is a tertiary group and R comprises a functional group X, with a water soluble, non-peptidic polymer POLY-Y, where Y is a functional group which reacts with X to form a covalent bond, to form a tertiary ester of the polymer; and (ii) treating the tertiary ester of the polymer with a strong base, such as an alkali metal hydroxide, in aqueous solution, to form a carboxylate salt of the polymer. The method may further comprise the step of (iii) treating the carboxylate salt of the polymer with an inorganic acid in aqueous solution, to convert the carboxylate salt to a carboxylic acid, thereby forming a carboxylic acid functionalized polymer. The carboxylic acid functionalized polymer can then be extracted from the aqueous solution with a suitable solvent, preferably a chlorinated solvent.

In one embodiment, X is a leaving group, such as a halide or a sulfonate ester, and Y is a hydroxyl group. When Y is a hydroxyl group, the reaction (i) is preferably carried out in the presence of a base, e.g. a base of the form $R'O^-M^+$, where M+ is a cation.

The treatment with strong base in reaction (ii) is preferably effective to produce a reaction pH of about 11 to 13.

The inorganic acid, e.g. a mineral acid, in step (iii) is preferably an acid that produces non-nucleophilic anions in aqueous solution. Preferred acids include sulfuric acid, nitric acid, phosphoric acid, and hydrochloric acid. The acid treatment of (iii) is preferably effective to produce a reaction pH of about 1 to 3.

The tertiary ester reagent employed in reaction (i) preferably has the structure (I):

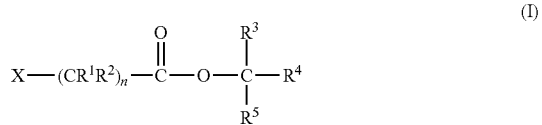
(I)

In structure (I), X is a leaving group; and each of $R^1$ and $R^2$ is independently selected from hydrogen, alkyl, cycloalkyl, alkoxy, aryl, aralkyl, and heterocycle. Preferably, the group $(CR^1R^2)_n$ does not include two heteroatoms attached to the same carbon atom; for example, $R^1$ and $R^2$ on the same carbon atom are preferably not both alkoxy. Each of $R^3$-$R^5$ is independently selected from lower alkyl, aryl, aralkyl, and cycloalkyl, where any of $R^3$-$R^5$ may be linked to form a ring or ring system, such as adamantyl. Any of $R^1$ to $R^5$, excepting hydrogen, may be substituted with a group selected from lower alkyl, lower alkoxy, C3-C6 cycloalkyl, halo, cyano, oxo(keto), nitro, and phenyl. The variable n is 1 to about 24, preferably 1 to 6, more preferably 1 to 4, and most preferably 1 or 2. In one embodiment, n is 1.

In selected embodiments of structure (I), each of $R^1$ and $R^2$ is independently hydrogen or unsubstituted lower alkyl, preferably hydrogen or methyl, and each of $R^3$ to $R^5$ is independently unsubstituted lower alkyl or phenyl, preferably methyl, ethyl, or phenyl. In one embodiment, each of $R^1$ and $R^2$ is H and n is 1.

The leaving group X in structure (I) is preferably a halide or a sulfonate ester. In one embodiment, the tertiary ester reagent is a tertiary alkyl haloacetate, such as a t-butyl haloacetate.

The water soluble, non-peptidic polymer is preferably selected from the group consisting of poly(alkylene glycols), poly(olefinic alcohol), poly(vinylpyrrolidone), poly(hydroxyalkylmethacrylamide), poly(hydroxyalkylmethacrylate), poly(saccharides), poly(α-hydroxyacetic acid), poly(acrylic acid), poly(vinyl alcohol), polyphosphazene, polyoxazolines, poly(N-acryloylmorpholine), and copolymers or terpolymers thereof. In a preferred embodiment, the polymer is a poly(ethylene glycol). The poly(ethylene glycol) may be linear and terminated at one end with the functional group Y and at the other end with another functional group Y' or a capping group, such as a methoxy group. Alternatively, the poly(ethylene glycol) may be branched, forked, or multiarmed.

The method may further comprise converting the carboxylic acid of the carboxylic acid functionalized polymer to an activated carboxylic acid derivative, e.g. an activated ester, such as, for example, an N-succinimidyl ester, o-, m-, or p-nitrophenyl ester, 1-benzotriazolyl ester, imidazolyl ester, or N-sulfosuccinimidyl ester. The polymer can then be conjugated with a biologically active molecule, by reacting the carboxylic acid derivative with a functional group, preferably a nucleophilic group such as a hydroxyl, thiol, or amino group, on the biologically active molecule. Preferably, the nucleophilic group is an amino group.

In a preferred embodiment of the method, as noted above, the polymer is a PEG polymer. In this aspect, the invention provides a method for preparing a poly(ethylene glycol) (PEG) functionalized with a carboxyl group, the method comprising:

(i) reacting a tertiary ester reagent R(C=O)OR', where R' is a tertiary alkyl group and R comprises a functional group X, with a polymer PEG-Y, where Y is a functional group which reacts with X to form a covalent bond, to form a PEG tertiary ester; and (ii) treating the PEG tertiary ester with a strong base, such as an alkali metal hydroxide, in aqueous solution, to form a PEG carboxylate salt. The method may further comprise (iii) treating the PEG carboxylate salt with an inorganic acid in aqueous solution, to convert the carboxylate salt to a carboxylic acid, thereby forming a PEG carboxylic acid. Preferred embodiments of the method correspond to those described above. The method may further comprise converting the PEG-carboxylic acid to an activated carboxylic acid derivative, such as an activated ester, and conjugating the polymer to a biologically active molecule, by reacting the carboxylic acid derivative with a functional group on the molecule, as described above.

In one embodiment, the poly(ethylene glycol) is linear and is terminated at one end with the functional group Y and at the other end with another functional group Y' or with a capping group, such as a methoxy group. The molecular weight of the PEG is preferably in the range of about 100 Da to about 100 kDa, more preferably in the range of about 300 Da to about 40, 50, or 60 kDa. In other embodiments, the PEG is branched, forked, or multiarmed, as described further below.

In a related aspect, the invention provides an isolated polymer product comprising a carboxylic acid functionalized polymer, made by the method disclosed herein, wherein the product contains less than 5% by weight of the starting material; that is, the POLY-Y or PEG-Y polymer, with the balance consisting essentially of the carboxylic acid functionalized polymer. Preferably, the isolated polymer product contains less than 2%, more preferably less than 1%, and most preferably less than 0.5% by weight of POLY-Y or PEG-Y polymer. In further preferred embodiments, the isolated polymer product contains less than 0.4%, more preferably less than 0.3%, and most preferably less than 0.2% by weight of POLY-Y or PEG-Y polymer.

In a further preferred aspect, the isolated polymer product contains substantially no amount of low molecular weight organic acid. In one embodiment, the isolated polymer product contains substantially no amount of monomeric organic carboxylic acid, such as trifluoroacetic acid.

In one embodiment of the polymer product of the invention, the carboxylic acid functionalized polymer is a PEG carboxylic acid. For example, the carboxylic acid functionalized polymer may be mPEG-$CH_2$—COOH, and contains less than 5%, preferably less than 2%, more preferably less than 0.5%, and most preferably less than 0.2% by weight of mPEG-OH. Preferably, the product contains substantially no amount of trifluoroacetic acid.

In another embodiment of the product, the carboxylic acid functionalized polymer is HOOC—$CH_2$-PEG-$CH_2$—COOH, and contains less than 5%, preferably less than 2%, more preferably less than 0.5%, and most preferably less than 0.2% by weight of HO-PEG-OH. Preferably, the product contains substantially no amount of trifluoroacetic acid.

In a further embodiment of the product, the carboxylic acid functionalized polymer is a multifunctional branched or multiarm carboxylic acid functionalized PEG represented by PEG-(CH$_2$—COOH)$_x$, where x is 3 to 8, and contains less than 5%, preferably less than 2%, more preferably less than 0.5%, and most preferably less than 0.2% by weight of PEG-(OH)$_x$. Preferably, the product contains substantially no amount of trifluoroacetic acid.

The invention further provides an improvement in a method of preparing a poly(ethylene glycol) (PEG)polymer functionalized with a carboxyl group, by reaction of a tertiary ester reagent R(C═O)OR', where R' is a tertiary alkyl group and R comprises a functional group X, with a polymer PEG-Y, where Y is a functional group which reacts with X to form a covalent bond, to form a PEG tertiary ester. The improvement comprises treating the PEG tertiary ester with a strong base, preferably an alkali metal hydroxide, in aqueous solution, to form a PEG carboxylate salt. The strong base is preferably one that is strong base is effective to produce a reaction pH of about 11 to 13 in the aqueous solution.

The improved method may further comprise treating the PEG carboxylate salt with an inorganic acid in aqueous solution, to convert the carboxylate salt to a carboxylic acid, thereby forming a PEG carboxylic acid. The inorganic acid is preferably a mineral acid selected from the group consisting of sulfuric acid, nitric acid, phosphoric acid, and hydrochloric acid.

These and other objects and features of the invention will become more fully apparent when the following detailed description of the invention is read in conjunction with the included drawings.

DETAILED DESCRIPTION OF THE INVENTION

The present invention now will be described more fully. This invention may, however, be embodied in many different forms and should not be construed as limited to the embodiments set forth herein; rather, these embodiments are provided so that this disclosure will be thorough and complete, and will fully convey the scope of the invention to those skilled in the art. The invention is not limited to the particular polymers, synthetic techniques, active agents, and the like set forth in this description, as such may vary within the scope of the invention as embodied by the appended claims. The terminology used herein is for describing particular embodiments only, and is not intended to be limiting.

I. DEFINITIONS

In describing and claiming the present invention, the following terminology will be used in accordance with the definitions described below.

As used in this specification, the singular forms "a," "an," and "the" include plural referents unless the context clearly dictates otherwise.

As used herein, "non-peptidic" refers to a polymer substantially free of peptide linkages. However, the polymer may include a minor number of peptide linkages spaced along the length of the backbone, such as, for example, no more than about 1 peptide linkage per about 50 monomer units.

"PEG" or "polyethylene glycol," as used herein, is meant to encompass any water-soluble poly(ethylene oxide). Typically, PEGs for use in the present invention will comprise one of the two following structures: —O(CH$_2$CH$_2$O)$_m$— or —CH$_2$CH$_2$—O—(CH$_2$CH$_2$O)$_m$—CH$_2$CH$_2$—, where m is generally from 3 to about 3000. In a broader sense, "PEG" can refer to a polymer that contains a majority, i.e. greater than 50%, of subunits that are —CH$_2$CH$_2$O—.

The terminal groups and architecture of the overall PEG may vary. The PEG may contain an end-capping group on a terminal oxygen which is generally a carbon-containing group typically comprised of 1-20 carbons and is preferably selected from alkyl, alkenyl, alkynyl, aryl, aralkyl, cycloalkyl, heterocyclo, and substituted forms of any of the foregoing. The end-capping group can also be a silane. Most preferred are alkyl(alkoxy) or aralkyl(aralkoxy) capping groups, such as methyl, ethyl or benzyl.

The end-capping group can also advantageously comprise a detectable label. Such labels include, without limitation, fluorescers, chemiluminescers, moieties used in enzyme labeling, colorimetric (e.g., dyes), metal ions, radioactive moieties, and the like.

The other ("non-end-capped") terminus is a typically hydroxyl, amine or an activated group that can be subjected to further chemical modification.

Specific PEG forms for use in the invention include PEGs having a variety of molecular weights, structures or geometries (e.g., branched, linear, forked, multiarmed).

A "multifunctional" polymer has 3 or more functional groups, which may be the same or different. Multifunctional polymers will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups.

A "difunctional" polymer has two functional groups contained therein, which may be the same (i.e., homodifunctional) or different (i.e., heterodifunctional).

"Molecular mass" or "molecular weight" refers to the average molecular mass of a polymer, typically determined by size exclusion chromatography, light scattering techniques, or intrinsic velocity determination in 1,2,4-trichlorobenzene. Unless otherwise noted, molecular weight is expressed herein as number average molecular weight (M$_n$), which is defined as ΣNiMi/ΣNi, wherein Ni is the number of polymer molecules (or the number of moles of those molecules) having molecular weight Mi.

The polymers of the invention, or employed in the invention, are typically polydisperse; i.e., the number average molecular weight and weight average molecular weight of the polymers are not equal. The polydispersity values, expressed as a ratio of weight average molecular weight (Mw) to number average molecular weight (Mn), (Mw/Mn), are generally low; that is, less than about 1.2, preferably less than about 1.15, more preferably less than about 1.10, still more preferably less than about 1.05, yet still most preferably less than about 1.03, and most preferably less than about 1.025.

An "activated carboxylic acid" refers to a functional derivative of a carboxylic acid that is more reactive than the parent carboxylic acid, particularly with respect to nucleophilic attack. Activated carboxylic acids include but are not limited to acid halides (such as acid chlorides), anhydrides, and esters.

More generally, the term "activated" or "reactive", when used in conjunction with a particular functional group, refers to a functional group that reacts readily with an electrophile or a nucleophile on another molecule, in contrast to groups that require strong catalysts or impractical reaction conditions in order to react (i.e., "nonreactive" or "inert" groups).

The term "protecting group" or "protective group" refers to a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., Protective Groups in Organic Synthesis, 3rd ed., John Wiley & Sons, New York, N.Y. (1999). As used herein, the term "functional group" or any synonym thereof is meant to encompass protected forms thereof.

The term "spacer" or "spacer moiety" refers to an atom or a collection of atoms used to link interconnecting moieties, such as a terminus of a water-soluble polymer portion and an electrophile. A typical spacer includes bonds selected from alkylene (carbon-carbon), ether, amino, amide, ester, carbamate, urea, and keto, and combinations thereof. A spacer may include short alkylene moieties alternating with, or flanked by, one or more types of heteroatom-containing linkages listed above. Various examples include —$CH_2OCH_2CH_2CH_2$—, —$CH_2C(O)NHCH_2$—, —$C(O)OCH_2$—, —$OC(O)NHCH_2CH_2$—, —$CH_2CH_2NHCH_2$, —$CH_2CH_2C(O)CH_2CH_2$—, —$CH_2CH_2CH_2C(O)NHCH_2CH_2NH$—, and —$CH_2CH_2CH_2C(O)NHCH_2CH_2NHC(O)CH_2CH_2$—. The spacer moieties of the invention may be hydrolytically stable or may include a physiologically hydrolyzable or enzymatically degradable linkage (e.g. an ester linkage).

"Alkyl" refers to a hydrocarbon chain, typically ranging from about 1 to 20 atoms in length. Such hydrocarbon chains are preferably but not necessarily saturated and may be branched or, preferably, linear (unbranched). Exemplary alkyl groups include ethyl, propyl, butyl, pentyl, 2-methylbutyl, 2-methylpropyl(isobutyl), 3-methylpentyl, and the like. As used herein, "alkyl" includes cycloalkyl when three or more carbon atoms are referenced.

"Lower alkyl" refers to an alkyl group containing from 1 to 6 carbon atoms, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

As used herein, "alkenyl" refers to a branched or unbranched hydrocarbon group having 2 to 15 carbon atoms and containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group having 2 to 15 atoms and containing at least one triple bond, such as ethynyl, n-propynyl, isopentynyl, n-butynyl, octynyl, decynyl, and so forth.

"Alkoxy" refers to an —OR group, wherein R is alkyl or substituted alkyl, preferably C1-C20 alkyl (e.g., methoxy, ethoxy, propyloxy, etc.), more preferably lower alkyl (i.e. C1-C6).

"Aryl" refers to a substituted or unsubstituted monovalent aromatic radical having a single ring (e.g., phenyl) or two condensed or fused rings (e.g., naphthyl). Multiple aryl rings may also be unfused (e.g. biphenyl). The term includes heteroaryl groups, which are aromatic ring groups having one or more nitrogen, oxygen, or sulfur atoms in the ring, such as furyl, pyrrole, pyridyl, and indole.

"Aralkyl" refers to an alkyl, preferably lower ($C_1$-$C_4$, more preferably $C_1$-$C_2$) substituent which is further substituted with an aryl group; examples are benzyl and phenethyl.

"Aralkoxy" refers to a group of the form —OR where R is aralkyl; one example is benzyloxy.

A "heterocycle" refers to a ring, preferably a 5- to 7-membered ring, whose ring atoms are selected from the group consisting of carbon, nitrogen, oxygen and sulfur. Preferably, the ring atoms include 3 to 6 carbon atoms. Examples of aromatic heterocycles (heteroaryl) are given above; non-aromatic heterocycles include, for example, pyrrolidine, piperidine, piperazine, and morpholine.

A "substituted" group or moiety is one in which a hydrogen atom has been replaced with a non-hydrogen atom or group, which is preferably a non-interfering substituent.

"Non-interfering substituents" are those groups that, when present in a molecule, are typically non-reactive with other functional groups contained within the molecule. These include, but are not limited to, lower alkyl, alkenyl, or alkynyl; lower alkoxy; C3-C6 cycloalkyl; halo, e.g., fluoro, chloro, bromo, or iodo; cyano; oxo (keto); nitro; and phenyl.

A "tertiary group" is a group of the form —$CR_3$, where each R is an organic moiety linked to C via a carbon atom. Each R may be, for example, alkyl, cycloalkyl, aryl, or aralkyl, substituted or unsubstituted. Examples of tertiary groups include t-butyl, where each R is methyl; triphenylmethyl (trityl), where each R is phenyl; and dimethoxytrityl (DMT), where two R's are p-methoxyphenyl and one is phenyl. Also included are groups where one or more R's form a ring or ring system, such as adamantyl.

A "tertiary ester" is an ester having a tertiary group as its alcohol portion; i.e. R'—(C=O)—$OCR_3$, where $CR_3$ is a "tertiary group" as defined above, and R' is the acid portion of the ester.

A "carboxyl group" as used herein refers to the group —C(=O)OH (carboxylic acid) or —C(=O)O$^-$M$^+$, where M$^+$ is a positively charged ion, such as an alkali metal ion (carboxylate group).

A "low molecular weight" organic acid refers to an acidic organic compound having a molecular weight less than about 400, preferably less than about 300, and more preferably less than about 200. The term typically refers to a non-polymeric and non-oligomeric acid, and generally refers to an acid used as a reagent. Examples include formic acid, acetic acid, trifluoroacetic acid (TFA), and p-toluenesulfonic acid.

An "electrophile" is an atom or collection of atoms having an electrophilic center, i.e., a center that is electron-seeking or capable of reacting with a nucleophile.

A "nucleophile" refers to an atom or a collection of atoms having a nucleophilic center, i.e., a center that is seeking an electrophilic center or capable of reacting with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, and orthoesters.

An "enzymatically degradable linkage" is a linkage that is subject to degradation by one or more enzymes.

A "hydrolytically stable" linkage or bond refers to a chemical bond, typically a covalent bond, that is substantially stable in water; i.e. it does not undergo hydrolysis under physiological conditions to any appreciable extent over an extended period of time. Generally, a hydrolytically stable linkage is one that exhibits a rate of hydrolysis of less than about 1-2% per day under physiological conditions. Examples of hydrolytically stable linkages include carbon-carbon bonds, ethers, amines, and amides. Hydrolysis rates of representative chemical bonds can be found in most standard chemistry textbooks.

A product containing "substantially no amount" of a specified component either contains no amount of the specified component, or contains an amount which is undetectable by conventional methods of analysis of the product, and/or has no detectable effect on the properties or stability of the product. For example, a product which has never knowingly or deliberately been exposed to or contacted with a particular substance would be considered to contain substantially no amount of the substance.

Each of the terms "drug," "biologically active molecule," "biologically active moiety," and "biologically active agent", when used herein, means any substance which can affect any physical or biochemical property of a biological organism, where the organism may be selected from viruses, bacteria, fungi, plants, animals, and humans. In particular, as used herein, biologically active molecules include any substance intended for diagnosis, cure mitigation, treatment, or prevention of disease in humans or other animals, or to otherwise enhance physical or mental well-being of humans or animals. Examples of biologically active molecules include, but are not limited to, peptides, proteins, enzymes, small molecule drugs, dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, antiviral agents, anti-inflammatory agents, anti-tumor agents, cardiovascular agents, anti-anxiety agents, hormones, growth factors, steroidal agents, and the like. Also included are foods, food supplements, nutrients, nutriceuticals, drugs, vaccines, antibodies, vitamins, and other beneficial agents.

The term "conjugate" refers to an entity formed as a result of covalent attachment of a molecule, e.g., a biologically active molecule, to a reactive polymer molecule, preferably a poly(ethylene glycol).

"Pharmaceutically acceptable excipient" or "pharmaceutically acceptable carrier" refers to an excipient that can be included in the compositions of the invention and that causes no significant adverse toxicological effects to a patient.

"Pharmacologically effective amount," "physiologically effective amount," and therapeutically effective amount" are used herein to refer to mean the amount of a polymer-active agent conjugate present in a pharmaceutical preparation that is needed to provide a desired level of active agent and/or conjugate in the bloodstream or in the target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

The term "patient" refers to a living organism suffering from or prone to a condition that can be prevented or treated by administration of a biologically active agent or conjugate thereof, and includes both humans and animals.

II. METHOD OF PREPARING CARBOXYLIC ACID FUNCTIONALIZED POLYMERS

A. Overview

The present invention provides, in one aspect, a method of preparing a water soluble, non-peptidic polymer functionalized with a carboxyl group, i.e. a carboxylate salt or carboxylic acid. The method involves reacting a tertiary ester reagent R(C=O)OR', where R' is a tertiary group, as defined above, and R includes a functional group X, with a water soluble, non-peptidic polymer POLY-Y, where Y is a functional group which reacts with X to form a covalent bond, to form a tertiary ester of the polymer, which may be represented as POLY-R—(C=O)OR'. The nature of the linkage between POLY and R depends on the functional groups Y and X.

The starting material of the reaction, represented by POLY-Y, or by PEG-Y when the polymer is a polyethylene glycol, may include more than one functional group Y, in various configurations. Examples include linear, branched, and multiarmed PEGs containing multiple hydroxyl groups, as discussed further below. The product of the reaction, i.e. the carboxyl-functionalized polymer, contains a number of carboxyl groups which is equal to the number of functional groups Y in the starting material (or greater than Y, if the starting material has existing carboxyl groups).

Preferably, the functional group Y of the polymer is a hydroxyl group, or other nucleophilic group, and the functional group X of the tertiary ester reagent is a leaving group capable of being displaced by Y. Other possible functional group combinations are described below.

Once the tertiary ester group is attached to the polymer, it is converted to a carboxylate by base hydrolysis in aqueous solution, which is preferably followed by acidification to produce the carboxylic acid. Surprisingly, it has been found that the tertiary ester, while stable in the presence of the base used in the initial nucleophilic substitution reaction, can be removed by base-promoted hydrolysis. As noted above, tertiary alkyl esters, such as t-butyl esters, are conventionally thought to be resistant to base hydrolysis.

The general reaction scheme below depicts a preferred embodiment of the method of the invention, where Y is hydroxyl and X is a leaving group, and the ester reagent has the structure shown as (I).

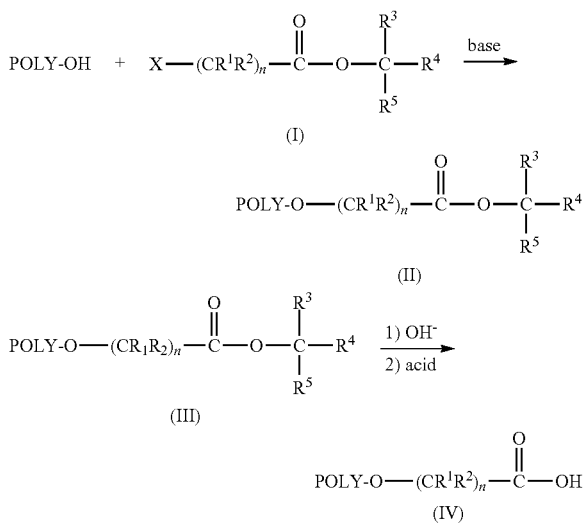

B. Reaction Components

In the preferred ester reagent (I), each of $R^1$ and $R^2$ is independently selected from H, lower alkyl, cycloalkyl, alkoxy, aryl, aralkyl, and heterocycle; and each of $R^3$-$R^5$ is independently selected from lower alkyl, aryl, and aralkyl, each as defined above. Preferably, the group $(CR^1R^2)_n$ does not include two heteroatoms attached to the same carbon atom; for example, $R^1$ and $R^2$ on the same carbon atom are preferably not both alkoxy. Any of $R^1$ to $R^5$, excepting hydrogen, may be substituted with a non-interfering substituent, as defined above.

Preferably, each of $R^1$ and $R^2$ is independently hydrogen or unsubstituted lower alkyl, and each of $R^3$ to $R^5$ is independently unsubstituted lower alkyl or phenyl. In selected embodiments, each of $R^1$ and $R^2$ is independently hydrogen or methyl, more preferably hydrogen, and each of $R^3$ to $R^5$ is independently methyl, ethyl, or phenyl.

The variable n is 1 to about 24, preferably 1 to about 12. In selected embodiments, n is 1 or 2, 1 to 3, 1 to 4, 1 to 5, 1 to 6, 1 to 7, 1 to 8, 1 to 9, 1 to 11, 1 to 12, 1 to 13, 1 to 14, 1 to 15, 1 to 16, 1 to 17, 1 to 18, 1 to 19, 1 to 20, 1 to 21, 1 to 22, 1 to 23, or 1 to 24. In further selected embodiments, n is 1 to 6; preferably, n is 1 to 4; and more preferably, n is 1 or 2. When n is greater than 1, the moiety —$(CR^1R^2)_n$— preferably includes at most two, and more preferably at most one, non-hydrogen embodiment of $R^1$ or $R^2$.

In further embodiments, n is 1, and $R^1$ and $R^2$ are independently hydrogen or methyl. In one such embodiment, when both $R^1$ and $R^2$ are hydrogen, the product (IV) contains a carboxymethyl group.

Preferably, the functional group X on the ester reagent (II) is a leaving group, such as halo, e.g. chloro or bromo, or sulfonate ester, such as p-toluenesulfonyl (tosyl), methanesulfonyl (mesyl), trifluorosulfonyl, or trifluoroethylsulfonyl (tresyl). However, other functional groups capable of reacting with a functional group on the polymer, to form a covalent linkage, could also be used. Preferably, the functional group on the polymer is a nucleophilic group, such as amine, hydrazide (—C(=O)NHNH$_2$), or thiol, and the functional group X on the ester reagent is an electrophilic group. In addition to leaving groups such as those described above, electrophilic groups include carboxylic ester, including imide ester, orthoester, carbonate, isocyanate, isothiocyanate, aldehyde, ketone, thione, alkenyl, acrylate, methacrylate, acrylamide, sulfone, maleimide, disulfide, iodo, epoxy, thiosulfonate, silane, alkoxysilane, halosilane, and phosphoramidate. More specific examples of these groups include succinimidyl ester or carbonate, imidazolyl ester or carbonate, benzotriazole ester or carbonate, p-nitrophenyl carbonate, vinyl sulfone, chloroethylsulfone, vinylpyridine, pyridyl disulfide, iodoacetamide, glyoxal, and dione. Also included are other activated carboxylic acid derivatives, as well as hydrates or protected derivatives of any of the above moieties (e.g. aldehyde hydrate, hemiacetal, acetal, ketone hydrate, hemiketal, ketal, thioketal, thioacetal). Preferred electrophilic groups include succinimidyl carbonate, succinimidyl ester, maleimide, benzotriazole carbonate, glycidyl ether, imidazoyl ester, p-nitrophenyl carbonate, acrylate, aldehyde, and orthopyridyl disulfide.

In general, the functional group X on the reagent is chosen such that it reacts with the functional group Y on the polymer much more readily than the functional group Y would react with the t-butyl ester portion of the reagent. When the polymeric functional group Y is a nucleophile, such as hydroxyl, X is most suitably a good leaving group such as halo or sulfonate ester.

Particularly preferred ester reagents include t-butyl haloacetates, such as t-butyl bromoacetate, t-butyl chloroacetate, and t-butyl iodoacetate. Such t-butyl haloacetates are available, for example, from Sigma Chemical Co., St. Louis, Mo.

In Scheme I, POLY-OH is a water soluble, non-peptidic polymer, such as, for example, mPEG-OH. In general, the polymer can be any water soluble, non-peptidic polymer, having any available geometric configuration (e.g., linear, branched, forked, etc.), as discussed further below. For the sake of simplicity, the reaction scheme given above utilizes a polymer with a single hydroxyl group. However, as would be appreciated by one of ordinary skill in the art, the polymer may comprise more than one hydroxyl group, such as 1 to about 25 hydroxyl groups (e.g., 1, 2, 3, 4, 5, 6, 7, 8, 9, 10 or more hydroxyl groups). Also, the hydroxyl group could be replaced with any nucleophilic functional group reactive with the functional group X on the tertiary ester reagent. Such nucleophilic functional groups include thiols, amines, and stabilized carbanions.

C. Reaction Process

For the first stage of the process, shown in the top line of exemplary Scheme I above, the components are preferably dissolved in a suitable organic solvent, such as t-butanol, benzene, toluene, xylenes, tetrahydrofuran (THF), dimethylformamide (DMF), dimethylsulfoxide (DMSO) and the like.

As shown in the embodiment of the invention represented by Scheme I, reaction of a polymeric hydroxyl group with the tertiary ester reagent is typically carried out in the presence of a base. Exemplary bases include potassium t-butoxide, butyl lithium, sodium amide, and sodium hydride. Other strong bases could also be used.

The reaction is typically carried out at a temperature of about 0-120° C., preferably about 20-80° C., more preferably about 25-50° C., although reaction conditions will vary based on the polymer and the functional groups reacting. As shown in the Examples provided below, reactions of hydroxy-containing PEGs with t-butyl bromoacetate were effectively carried out at temperatures between room temperature and about 45° C.

The reaction time is typically about 0.5 hours to about 24 hours; e.g. about 1 to 20, 3 to 18, 4 to 12, or 6 to 8 hours. Typical reaction times for reaction of a hydroxylated polymer with t-butyl bromoacetate, as shown in the Examples below, are in the range of 12 to 20 hours. The reaction may be monitored for completion according to standard methods. Preferably, the reaction is carried out under an inert atmosphere such as nitrogen or argon.

The reaction preferably employs a molar excess of the ester reagent (e.g., a twofold, threefold, 6 fold, 10 fold, or 20 fold, up to about 30 fold molar excess), in order to ensure that complete conversion of the polymer starting material is achieved. Following this stage of the reaction, the organic solvent is removed, typically by evaporation or distillation.

The ester-containing product (III) is dissolved in water, preferably distilled or deionized water, for the second stage of the process, in which the ester-containing polymer is subjected to base-promoted hydrolysis by treatment with a strong base, such as hydroxide, in aqueous solution. The base hydrolysis is typically carried out at a pH to about 9 or above, preferably about 10 or above, and more preferably about 11 or above (e.g., about 11 to about 13). Accordingly, the base is one that is strong enough to produce a pH in this range in aqueous solution. In one embodiment, the pH is adjusted to fall in the range from about 12 to about 12.5. Preferably, base is added as necessary throughout the reaction to maintain the pH in this range. The base is also effective to hydrolyze any remaining ester reagent.

The base should produce a highly water soluble salt when neutralized with acid in the step subsequent to hydrolysis. Preferred are alkali metal hydroxides, such as sodium hydroxide (NaOH) or potassium hydroxide (KOH).

The use of distilled or deionized water, or water having no detectable levels of divalent cations such as calcium and magnesium ions, is also preferred. The base hydrolysis step is typically conducted at a temperature of about 0-50° C., preferably about 10-30° C. The reaction time is typically about 12 to 36 hours; e.g. about 18 to 24 hours.

The polymer carboxylate salt produced by the base hydrolysis can be isolated and stored as the salt, or, preferably, it is directly converted to the carboxylic acid by treatment with acid, as described below. Generally, the carboxylic acid is more suitable for further derivatization than the carboxylate salt.

The carboxylate-containing polymer is treated with aqueous acid to convert the salt to the free acid form. The acid is preferably one that produces a non-nucleophilic anion in aqueous solution. Mineral acids (i.e., inorganic acids) are preferred, such as sulfuric acid, nitric acid, phosphoric acid, hydrochloric acid, and the like. Typically, sufficient acid is added to adjust the pH of the solution to about 1-3, more preferably about 2-3, which is effective to convert the polymer carboxylate salt to a free acid form, as well as to neutralize (and convert to a freely water soluble salt) any base remaining in solution. The acidification step is typically conducted at a temperature of about 0° to about 50° C., preferably about 10° to about 30° C.

The carboxylic acid-containing polymer is then separated using a conventional organic extraction step, preferably employing a halogenated solvent such as dichloromethane or chloroform. The polymer product is extracted into the organic phase, while any hydrolyzed reagent and excess mineral acid or its salt remains in the aqueous phase. Thus, separation of the mineral acid from the polymer product is relatively simple.

The organic extract is dried and concentrated, and the polymeric product is then purified using standard methods. For example, the polymer may be isolated by precipitation, followed by filtration and drying. The choice of precipitating solvent will depend on the nature of the polymer, for PEG polymers, as described in the Examples below, ethyl ether is a suitable precipitating solvent. Recrystallization from solvents such as ethyl acetate or ethanol can also be used for purification.

D. Reaction Products

Using the method of the invention, carboxyl-functionalized polymers are produced with high purity, typically with a purity of at least about 95%, preferably at least about 96%, 97%, or 98%, more preferably at least about 99%, and most preferably at least about 99.5% by weight. In selected embodiments, the polymer product contains at least about 99.6%, 99.7%, 99.8%, or 99.9% by weight of the desired carboxyl-functionalized polymer. Accordingly, the product of the synthetic method disclosed herein contains less than 5%, preferably less than 4%, 3%, or 2%, more preferably less than 1%, and most preferably less than 0.5% by weight of starting polymer (e.g., mPEG-OH, PEG diol, or multi-functional PEG polyol) or other polymeric impurities. In selected embodiments, the product contains less than 0.4%, 0.3%, 0.2% or 0.1% by weight of polymeric starting material (e.g., mPEG-OH) or other polymeric impurities.

By "product" or "polymer product" is meant the material obtained by carrying out the synthetic process disclosed above, including routine workup procedures such as extraction, precipitation and removal of solvent. As shown in the Examples below, reaction mixtures containing the products of the methods disclosed herein were worked up by extraction with a chlorinated solvent, followed by precipitation of the product from ethyl ether. Ion exchange chromatographic analysis of these products showed essentially 100% of the desired PEG-carboxylic acid product, with no detectable amount of starting material or other polymeric impurity present. Accordingly, polymer products having the above-disclosed purities are obtained without the need for removal of polymeric impurities, such as starting material. These products can often be used directly for further derivatization and/or conjugation, as described below. A further advantage of this process is that it provides high purity polymeric carboxylic acids, such as mPEG carboxylic acids, starting from inexpensive starting materials such as mPEG-OH, in contrast to the use of commercially available polymeric carboxylic acids, which tend to be expensive and frequently contain residual amounts of polymeric hydroxyl compound as well.

As described above, the reagents employed in the synthetic process disclosed herein are readily removed from the polymeric product. In particular, no low molecular weight organic acids, such as TFA, are used in the process. Accordingly, the carboxyl-containing polymer products of this invention contain no trace amounts of low molecular weight organic acids, such as TFA, as would commonly occur in polymeric carboxylic acids made using a hydrolysis process which employs such a reagent. The present products therefore do not suffer the disadvantage of reduced stability associated with the presence of residual acids, as described above. For example, the polymer described in Example 4 below showed no sign of degradation (by GPC analysis) after 8 months of storage at −20° C.

III. SUITABLE WATER-SOLUBLE NON-PEPTIDIC POLYMERS

Any of a variety of non-peptidic, water soluble polymers can be used in the present invention. The polymer should be non-toxic and biocompatible, meaning that it is capable of coexistence with living tissues or organisms without causing harm. Examples of suitable polymers include, but are not limited to, poly(alkylene glycols), copolymers of ethylene glycol and propylene glycol, poly(olefinic alcohol), poly (vinylpyrrolidone), poly(hydroxyalkylmethacrylamide), poly(hydroxyalkylmethacrylate), poly(saccharides), poly(α-hydroxyacetic acid), poly(acrylic acid), poly(vinyl alcohol), polyphosphazene, polyoxazolines, poly(N-acryloylmorpholine), such as described in U.S. Pat. No. 5,629,384, which is incorporated by reference herein in its entirety, and copolymers, terpolymers, and mixtures thereof.

The molecular weight of the polymer will vary depending on the desired application, the configuration of the polymer structure, the degree of branching, and the like. Generally, polymers having a molecular weight of about 100 Da to about 100,000 Da are useful in the present invention, preferably about 200 Da to about 60,000 Da, and more preferably about 300 Da to about 40,000 Da. Exemplary polymer embodiments have a molecular weight of approximately 200 Da, 350 Da, 550 Da, 750 Da, 1,000 Da, 2,000 Da, 3,000 Da, 4,000 Da, 5,000 Da, 7,500 Da, 10,000 Da, 15,000 Da, 20,000 Da, 25,000 Da, 30,000 Da, 35,000 Da, 40,000 Da, 50,000 Da, 55,000 Da, and 60,000 Da.

The polymer preferably comprises at least one hydroxyl group, capable of reacting with a tertiary ester reagent carrying a leaving group, as described herein, in a nucleophilic substitution reaction. However, other functional groups capable of reacting with a functional group of the tertiary ester reagent could also be used. These include other nucleophilic groups, such as amine, hydrazide (—C(=)NH$_2$), and thiol; and electrophilic groups, such as carboxylic ester, including imide ester, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halosilane, and phosphoramidate. More specific examples of these groups include succinimidyl ester or carbonate, imidazolyl ester or carbonate, benzotriazole ester or carbonate, p-nitrophenyl carbonate, vinyl sulfone, chloroethylsulfone, vinylpyridine, pyridyl disulfide, iodoacetamide, glyoxal, dione, mesylate, tosylate, and tresylate. Also included are other activated carboxylic acid derivatives, as well as hydrates or protected derivatives of any of the above moieties (e.g. aldehyde hydrate, hemiacetal, acetal, ketone hydrate, hemiketal, ketal, thioketal, thioacetal). Preferred electrophilic groups include succinimidyl carbonate, succinimidyl ester, maleimide, benzotriazole carbonate, glycidyl ether, imidazoyl ester, p-nitrophenyl carbonate, acrylate, tresylate, aldehyde, and orthopyridyl disulfide.

The functional groups are selected such that a nucleophilic group on the polymer reacts with an electrophilic group on the tertiary ester reagent, or vice versa. The reaction between the two functional groups is preferably a displacement reaction of a leaving group by a nucleophile, but could also be, for example, a condensation or addition reaction.

The polymer preferably comprises at least one nucleophilic group, such as a hydroxyl group. For ease of reference, hydroxyl groups are discussed below, although other functional groups could be used. A polymer may also include different functional groups within the same molecule. Preferably these have similar functionality, e.g. both nucleophilic, such as a hydroxyl group and an amino group.

Preferably, the polymer is a poly(ethylene glycol) (i.e., PEG) polymer. As noted above, the term PEG includes poly(ethylene glycol) in any of a number of geometries or forms, including linear forms, branched or multi-arm forms (e.g., forked PEG or PEG attached to a polyol core), pendant PEG, or PEG with degradable linkages therein.

The number and position of hydroxyl groups (and/or other functional groups) carried by the polymer may vary. Typically, the polymer comprises 1 to about 25 hydroxyl groups, preferably 1, 2, 3, 4, 5, 6, 7, 8, 9, or 10 hydroxyl groups. Linear polymers, such as linear PEG polymers, typically comprise one or two hydroxyl groups, each positioned at a terminus of the polymer chain. If the PEG polymer is monofunctional (i.e., mPEG), the polymer includes a single hydroxyl group. If the PEG polymer is difunctional, the polymer contains two hydroxyl groups, one at each terminus of the polymer chain, or it contains a single hydroxyl group and a different functional group at the opposing terminus. Multi-arm or branched polymers may comprise a greater number of hydroxyl groups.

Multi-armed or branched PEG molecules are described, for example, in U.S. Pat. No. 5,932,462, which is incorporated by reference herein in its entirety. Generally speaking, a multi-armed or branched polymer possesses two or more polymer "arms" extending from a central branch point, which preferably comprise a hydrolytically stable linking structure. An exemplary branched PEG polymer is methoxy poly(ethylene glycol) disubstituted lysine.

In another multi-arm embodiment, the polymer comprises a central core molecule derived from a polyol or polyamine, the central core molecule providing a plurality of attachments sites suitable for covalently attaching polymer arms to the core molecule in order to form a multi-arm polymer structure. Depending on the desired number of polymer arms, the polyol or polyamine will typically comprise 3 to about 25 hydroxyl or amino groups, preferably 3 to about 10, most preferably 3 to about 8 (e.g., 3, 4, 5, 6, 7, or 8).

Multi-armed polymers are further described, for example, in co-owned U.S. Patent Appn. Nos. 2002/0156047 and 2002/0156047, which are incorporated herein by reference.

The PEG polymer may alternatively comprise a forked PEG. Generally speaking, a polymer having a forked structure is characterized as having a polymer chain attached to two or more functional groups via covalent linkages extending from a hydrolytically stable branch point in the polymer. U.S. Pat. No. 6,362,254, the contents of which are incorporated by reference herein, discloses various forked PEG structures capable of use in the present invention.

The PEG polymer may also be a pendant PEG molecule, having reactive groups (e.g., hydroxyl groups) covalently attached along the length of the PEG backbone rather than at the end of the PEG chain. The pendant reactive groups can be attached to the PEG backbone directly or through a linking moiety, such as an alkylene group.

Different polymers can be incorporated into the same polymer backbone. For example, one or more of the PEG molecules in the branched structures described above can be replaced with a different polymer type.

The polymer can also be prepared with one or more hydrolytically stable or degradable linkages in the polymer backbone. For example, PEG can be prepared with ester linkages in the polymer backbone that are subject to hydrolysis. Other hydrolytically degradable linkages that may be incorporated include carbonate, imine, phosphate ester, hydrazone, acetal, orthoester, and phosphoramidate linkages.

The term poly(ethylene glycol) or PEG includes any or all the above described variations. Generally preferred PEG structures include linear monofunctional, branched monofunctional, and linear, branched or forked difunctional or trifunctional PEGs.

Because end-capped polyethylene glycol starting materials, such as mPEG (methoxy-PEG) or bPEG (benzyloxy-PEG), can contain detectable amounts of PEG diol impurity, leading to side products that are often difficult to analyze or separate, the PEG starting material is, in one preferred embodiment, a diol-free benzyloxy-PEG as described in co-owned U.S. Pat. No. 6,448,369.

IV. FURTHER DERIVATIZATION AND CONJUGATION OF CARBOXYLIC ACID FUNCTIONALIZED POLYMERS

A. Overview

If desired, a carboxylic acid functionalized polymer prepared by the method of the invention can be further modified to form useful reactive derivatives of carboxylic acids using methodology known in the art. Preparation of such derivatives is facilitated by the high purity of the carboxylic acid functionalized polymers of the invention, as compared to prior art products containing, for example, residual starting material polymer and/or residual reagents such as TFA. This is a significant benefit, particularly for a pharmaceutical product, since the presence and amounts of such contaminants can be highly variable, thus leading to irreproducibility of the product.

Accordingly, the method of the invention, wherein a carboxylic acid functionalized polymer is prepared, may further comprise the steps of (i) modifying the carboxylic acid to form a reactive derivative and (ii) conjugating the reactive derivative to a pharmacologically relevant molecule having a corresponding reactive functional group. The steps (i) and (ii) may be performed in situ, where the carboxylic acid is converted to an activated derivative using one of many activating reagents known in the art, then immediately reacted with the molecule to be conjugated.

The carboxylic acid can be derivatized to form, for example, acyl halides, acyl pseudohalides, such as acyl cyanide, acyl isocyanate, and acyl azide, neutral salts, such as alkali metal or alkaline-earth metal salts (e.g. calcium, sodium, or barium salts), esters, anhydrides, amides, imides, hydrazides, and the like. In a preferred embodiment, the acid is esterified to form an active ester, such as an N-succinimidyl ester, o-, m-, or p-nitrophenyl ester, 1-benzotriazolyl ester, imidazolyl ester, or N-sulfosuccinimidyl ester.

In one embodiment, the further derivatized polymer is a PEG polymer having the structure:

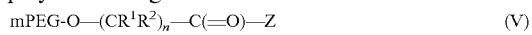
mPEG-O—(CR$^1$R$^2$)$_n$—C(=O)—Z (V)

wherein R$^1$, R$^2$ and n are as described above. The moiety Z is preferably selected from the group consisting of halo, amino, substituted amino, —NCO, —NCS, N$_3$, —CN, and —OR', wherein R' is selected from N-succinimidyl, nitrophenyl, benzotriazolyl, imidazolyl, N-sulfosuccinimidyl, N-phthalimidyl, N-glutarimidyl, N-tetrahydrophthalimidyl, N-norbornene-2,3-dicarboximidyl, and hydroxy-7-azabenzotriazolyl.

The carboxyl-containing polymer produced by the method of the invention, or a reactive derivative thereof, can be used to form conjugates with biologically active molecules, particularly biologically active molecules carrying nucleophilic functional groups, such as amino, hydroxyl, or mercapto (thiol) groups.

Frequently, the molecule to be conjugated is a protein. Proteins are conjugated via reactive amino acids, such as lysine, histidine, arginine, aspartic acid, glutamic acid, serine, threonine, tyrosine, cysteine, the N-terminal amino group, and the C-terminal carboxylic acid. Carbohydrate moieties on glycosylated proteins may also be employed as conjugation sites. For reaction with an activated carboxylic acid, the most suitable groups are the N-terminal amino group, amine-containing side chains on lysine, histidine, and arginine, hydroxyl-containing side chains on serine, threonine, and tyrosine, and thiol side chains on cysteine.

Although the preferred methods of conjugation of the carboxyl-containing polymers of the invention employ activated carboxylic acid derivatives, which react with nucleophilic groups on the molecule to be conjugated, it is also possible to derivatize the terminal carboxyl group to contain any variety of functional groups. For example, in one embodiment, the moiety Z in structure (V) above has the structure —NHR$_6$, wherein R$_6$ is an organic group that contains a reactive functional group (e.g., aldehyde, maleimide, mercapto, hydroxyl, amino, etc.), the functional group(s) being separated from the nitrogen atom by an alkylene chain (e.g., C1-6) and, optionally, an additional linker, such as a short PEG chain and another alkylene chain (e.g., alkylene-PEG-alkylene).

B. Exemplary Methods of Conjugation

Such polymer conjugates can be formed using known techniques for covalent attachment of an activated polymer, such as an activated PEG, to a biologically active agent. See, for example, Poly(ethylene glycol): Chemistry and Biological Applications, J. M. Harris and S. Zalipsky, editors, American Chemical Society, Washington, D.C. (1997) or Bioconjugate Techniques, G. T. Hermanson, Academic Press (1996). In general, conjugation reactions are typically carried out in a buffer, such as a phosphate or acetate buffer, at or near room temperature, although conditions will depend on the particular reaction being carried out. An excess of the polymeric reagent is typically combined with the active agent. In some cases, however, it is preferred to have stoichiometric amounts of the reactive groups on the polymeric reagent and on the active agent.

Progress of a conjugation reaction can be monitored by SDS-PAGE, MALDI-TOF mass spectrometry, or any other suitable analytical method. Once a plateau is reached with respect to the amount of conjugate formed or the amount of unconjugated polymer remaining, the reaction is assumed to be complete. The product mixture is purified, if necessary, to separate excess reagents, unconjugated reactants (e.g., active agent) undesired multi-conjugated species, and/or unreacted polymer, using known methods.

For example, conjugates having different molecular weights can be separated using gel filtration chromatography. Fractions may be analyzed by a number of different methods, e.g. (i) OD at 280 nm for protein content, (ii) BSA protein analysis, (iii) iodine testing for PEG content (Sims et al., Anal. Biochem. 107:60-63, 1980), or (iv) SDS-PAGE, followed by staining with barium iodide.

Separation of positional isomers (that is, conjugates of the same or substantially the same molecular weight having a polymer attached at different positions on a molecule) can be carried out by reverse phase HPLC or ion exchange chromatography.

The conjugated product may be lyophilized for storage, with or without residual buffer. In some instances, it is preferable to exchange a buffer used for conjugation, such as sodium acetate, for a volatile buffer, such as ammonium carbonate or ammonium acetate, that can be readily removed during lyophilization. Alternatively, a buffer exchange step may be used using a formulation buffer, so that the lyophilized conjugate is in a form suitable for reconstitution into a formulation buffer and ultimately for administration to a mammal.

C. Exemplary Agents for Conjugation

A biologically active agent for use in coupling to polymer formed by the method of the invention may be any one or more of the following. Suitable agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules, peptides, polypeptides, proteins, antibodies, polysaccharides, steroids, nucleotides, oligonucleotides, polynucleotides, fats, electrolytes, and the like. Preferably, an active agent for coupling to a carboxyl-containing polymer of the invention possesses a native amino, hydroxyl, or thiol group, or is modified to contain at least one such group.

Specific examples of active agents include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones, human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIc inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracehular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to a polymer include amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid, dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, granicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. The above biologically active proteins are additionally meant to encompass variants having one or more amino acids substituted (e.g., cysteine), deleted, or the like, as long as the resulting variant protein possesses at least a certain degree of activity of the parent (native) protein.

V. Pharmaceutical Compositions and Administration Methods

The present invention also includes pharmaceutical preparations comprising a conjugate as provided herein in combination with a pharmaceutical excipient. Exemplary excipients include, without limitation, those selected from the group consisting of carbohydrates, antimicrobial agents, antioxidants, surfactants, buffers, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfate, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient will be present in the composition in an amount of about 1% to about 99% by weight, preferably from about 5%-98% by weight, more preferably from about 15-95% by weight of the excipient, with concentrations less than 30% by weight most preferred.

The foregoing pharmaceutical excipients and others are described in *Remington: The Science & Practice of Pharmacy*, 19' ed., Williams & Williams, (1995), the *Physician's Desk Reference*, 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with conjugate, as determined by those skilled in the art. The method comprises administering, generally via injection, a therapeutically effective amount of the conjugate, preferably provided as part of a pharmaceutical preparation.

The actual dose to be administered will vary depend upon the age, weight, and general condition of the subject, as well as the severity of the condition being treated, the judgment of the health care professional, and the conjugate being administered. Therapeutically effective amounts of particular drugs are known to those skilled in the art and/or are described in the pertinent reference texts and literature. Generally, a therapeutically effective amount of conjugate will range from about 0.001 mg to 100 mg, preferably in doses from 0.01 mg/day to 75 mg/day, and more preferably in doses from 0.10 mg/day to 50 mg/day. The unit dosage of any given conjugate (again, preferably provided as part of a pharmaceutical preparation) can be administered in a variety of dosing schedules depending on the judgment of the clinician, needs of the patient, and so forth.

EXAMPLES

The following examples are provided to illustrate the invention but should not be considered in limitation of the invention. For example, although PEG is used in the Examples, the use of other water soluble, non-peptidic polymers is encompassed by the invention, as discussed above.

All PEG reagents referred to in these Examples are available from Nektar AL, Huntsville, Ala. All NMR data was generated by a 300 or 400 MHz NMR spectrometer manufactured by Bruker.

Example 1 illustrates reaction of mPEG-OH with tert-butyl bromoacetate in the presence of a base to form a tert-butyl ester terminated polymer. Thereafter, the polymer is subjected to base-promoted hydrolysis using NaOH as the base, followed by acidification using phosphoric acid, to form the final carboxylic acid terminated polymer.

Examples 2 and 3 exemplify similar reaction of a difunctional PEG starting material (PEG diol; HO-PEG-OH). Example 4 illustrates reaction of a multifunctional, 4-armed PEG starting material, based on a pentaerythritol core and having four reactive hydroxyls, one at the terminus of each PEG "arm".

Example 1 mPEG(30,000)-carboxylic acid

A solution of mPEG-30,000 (50 g, 0.00167 moles) (NOF Corporation) in toluene (600 ml) was azeotropically dried by distilling off 300 ml toluene. t-Butanol (70 ml), potassium tert-butoxide (95%, 1.75 g, 0.0148 moles, 8.9 fold excess) and tert-butyl bromoacetate (3.3 g, 0.0169 moles, 10.1 fold excess) were added, and the mixture was stirred overnight at 45° C. under argon atmosphere. The solvent was distilled off under reduced pressure, and the residue was dissolved in distilled water (1000 ml).

The pH of the aqueous solution was adjusted to 12 with 1 M sodium hydroxide, and the solution was stirred for 18 h, keeping the pH at 12 by periodic addition of 1M sodium hydroxide.

The pH was adjusted to 3 with 5% phosphoric acid, and the product was extracted with dichloromethane. The extract was dried with anhydrous magnesium sulfate and added to ethyl ether. The precipitated product was filtered off and dried under reduced pressure, giving a yield of 46.6 g.

NMR ($d_6$-DMSO): 3.24 ppm (s, —$OCH_3$), 3.51 ppm (s, PEG backbone), 4.01 ppm (s, —$CH_2$—COO—).

Anion exchange chromatographic analysis: mPEG(30,000)-carboxylic acid 100%. This analysis showed that essentially no starting material or other polymeric impurity was present in the ether-precipitated product.

Example 2

PEG(10,000)-dicarboxylic acid

PEG-10,000 (35.25 g, 0.00705 eq) (NOF Corporation) (terminated at both ends with hydroxyl) was dissolved in toluene (600 ml) and azeotropically dried by distilling off toluene. The residue was redissolved into anhydrous toluene (500 ml). tert-Butanol (40 ml), potassium tert-butoxide (4 g, 0.0356 moles, 5.1 fold excess) and anhydrous toluene (40 ml) were combined and added to the above reaction mixture, followed by stirring for about 3.5 hours. t-Butyl bromoacetate (7 ml, 0.0474 moles, 6.7 fold excess) was added, and the mixture was stirred overnight at 40.degree. C. under argon atmosphere. The solvent was distilled off under reduced pressure, and the residue was dissolved in distilled water (1000 ml).

The pH of the aqueous solution was adjusted to 12.1 with 1M sodium hydroxide, and the solution was stirred overnight, keeping the pH at 12.1 by periodic addition of 1M sodium hydroxide.

The pH was adjusted to 1.0 with 1M hydrochloric acid, and the product was extracted with dichloromethane. The extract was dried with anhydrous sodium sulfate, concentrated, and added to ethyl ether. The precipitated product was filtered off and dried under reduced pressure, to yield 33 g.

NMR ($d_6$-DMSO): 3.51 ppm (s, PEG backbone), 4.01 ppm (s, —$CH_2$—COO—).

Anion exchange chromatographic analysis: PEG(10,000)-dicarboxylic acid 100%.

Example 3

PEG(5,000)-dicarboxylic acid

A solution of PEG-5,000 (35 g, 0.01400 equivalents) (NOF Corporation) in acetonitrile (800 ml) was azeotropically dried by distilling off acetonitrile, and the residue was redissolved into anhydrous toluene (300 ml). t-Butanol (50 ml), potassium tert-butoxide (4.7 g, 0.0419 moles, 2.99 fold excess), and anhydrous toluene (50 ml) were combined and added to the above reaction mixture, followed by about 3.5 hours of stirring. t-Butyl bromoacetate (7.2 ml, 0.0488 moles, 3.48 fold excess) was added, and the mixture was stirred 20 hrs at room temperature under an argon atmosphere. The solvent was distilled off under reduced pressure, and the residue was dissolved in distilled water (1000 ml).

The pH of the aqueous solution was adjusted to 12.0 with 1M sodium hydroxide, and the solution was stirred overnight, keeping the pH at 12.0 by periodic addition of 1M sodium hydroxide.

The pH was adjusted to 2.0 with 1M hydrochloric acid and the product was extracted with dichloromethane. The extract was dried with anhydrous sodium sulfate, concentrated and added to ethyl ether. The precipitated product was filtered off and dried under reduced pressure, to yield 32 g.

NMR ($d_6$-DMSO): 3.51 ppm (s, PEG backbone), 4.01 ppm (s, —$CH_2$—COO—).

Anion exchange chromatographic analysis: PEG(5,000)-dicarboxylic acid 100%.

Example 4

4-Arm-PEG(10,000)-tetracarboxylic acid

A solution of Multi-arm PEG (4-Arm), MW 10 kDa (Nektar, Huntsville Ala.) (160 g, 0.064 equivalents) in toluene (2,300 ml) was azeotropically dried by distilling off 1,000 ml of toluene at 80° C. under reduced pressure. In another vessel, tert-butanol (17.3 ml) and potassium tert-butoxide (7.18 g, 0.128 moles, 2.00 fold excess) were mixed and then added to the dried toluene solution from above. The resulting solution was stirred for about 3.5 hours at 45° C. t-Butyl bromoacetate (20.8 ml, 0.141 moles, 2.20 fold excess) was added, and the mixture was stirred 12 hrs at 45° C. under an argon atmosphere. The solvent was distilled off under reduced pressure, and the residue was dissolved in distilled water (1,600 ml).

The pH of the aqueous solution was adjusted to 12.0 with 1M sodium hydroxide, and the solution was stirred for 17 hr while keeping the pH at 12.0 by periodic addition of 1M sodium hydroxide.

The pH was then adjusted to 1.5 with 1M phosphoric acid, and the product was extracted with dichloromethane. The extract was dried with anhydrous sodium sulfate, concentrated and added to ethyl ether. The precipitated product was filtered off and dried under reduced pressure, to yield 15.5 g.

NMR ($d_6$-DMSO): 3.51 ppm (s, PEG backbone), 4.01 ppm (s, —$CH_2$—COO—), substitution 100%.

After 8 months of storage at −20° C., GPC analysis was identical to the original product. Therefore, no detectable degradation occurred during storage.

Many modifications and other embodiments of the invention will come to mind to one skilled in the art to which this invention pertains having the benefit of the teachings presented in the foregoing description. Therefore, the invention is not to be limited to the specific embodiments disclosed, and modifications and other embodiments are intended to be included, within the scope of the appended claims.

What is claimed is:

1. A method for preparing a composition of carboxylic acid-functionalized polymers, the method comprising:
   i) reacting an ester reagent of the following structure,

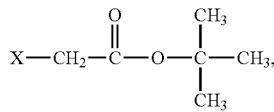

wherein X is sulfonate ester,
with a mPEG-OH to form a tertiary ester of the mPEG-OH of the following structure,

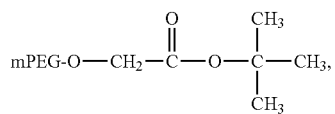

ii) treating the tertiary ester of the mPEG-OH with a strong base in aqueous solution to form a carboxylate salt; and
   iii) treating the carboxylate salt of the polymer with an inorganic acid in aqueous solution to convert the carboxylate salt to a carboxylic acid, thereby forming a carboxylic acid functionalized polymer of the following structure,

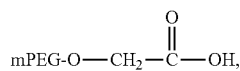

wherein the method results in a composition containing less than 5% by weight of mPEG-OH, with the balance consisting essentially of said carboxylic acid functionalized polymer.

2. The method of claim 1, wherein the composition contains less than 2% by weight of mPEG-OH.

3. The method of claim 1, wherein the composition contains less than 0.5% by weight of mPEG-OH.

4. The method of claim 1, wherein the composition contains substantially no amount of trifluoroacetic acid.

5. The method of claim 1, wherein the mPEG-OH has a molecular weight of about 100 Da to about 100,000 Da.

6. The method of claim 1, wherein the mPEG-OH has a molecular weight of about 200 Da to about 60,000 Da.

7. The method of claim 1, wherein the mPEG-OH has a molecular weight of about 300 Da to about 40,000 Da.

8. The method of claim 1, wherein the mPEG-OH has a molecular weight of about 5,000 Da.

9. The method of claim 1, wherein the mPEG-OH has a molecular weight of about 10,000 Da.

10. The method of claim 1, wherein the mPEG-OH has a molecular weight of about 20,000 Da.

11. The method of claim 1, wherein the mPEG-OH has a molecular weight of about 40,000 Da.

* * * * *